United States Patent [19]

Michelssen

[11] Patent Number: Plant 6,567

[45] Date of Patent: Jan. 31, 1989

[54] ACHIMENES PLANT NAMED TETRA LINDA

[75] Inventor: Konrad Michelssen, Hannover, Fed. Rep. of Germany

[73] Assignee: Mikkelsens, Inc., Ashtabula, Ohio

[21] Appl. No.: 62,948

[22] Filed: Jun. 16, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An Achimenes plant named Tetra Linda, characterized by its distinct all white flower color, including throat; vigorous and compact growth habit; floriferousness, producing many flowers on stiff stems which elevate the flowers above the leaf canopy; long flowering period, and by its ability to propagate well from rhizomes, leaf and stem cuttings.

1 Drawing Sheet

The present invention relates to a new and distinctive cultivar of Achimenes plant, botanically known as achimenes, and known by the cultivar name Tetra Linda.

Tetra Linda was discovered by me as a mutation of the cultivar India (a diploid) which was doubled in chromosome number with colchicine to produce the new tetraploid cultivar.

Asexual reproduction of leaf cuttings has shown that the unique features of this new streptocarpus are stabilized and are reproduced true to type in successive propagations.

The characteristics listed below distinguish Tetra Linda from both its parent and other cultivated achimenes of this type known and used in the floriculture industry. Several known cultivars are used for comparison purposes, with none of the comparison cultivars being patented. The cultivar Schneewitchen is a diploid and the cultivars Rosa Charma, Alrote Charm and Klaus Neubner are tetraploids. There are dipolid and tetraploid cultivars having the varietal designation India, with the present invention being a mutation of the diploid. All references below to that cultivar are to the tetraploid.

1. Tetra Linda has a distinct all white flower including the throat, while Schneewittchen has a white flower with a yellow throat on the lower 3 petals and a lavender-purple throat on the upper 2 petals.

2. Tetra Linda has a flower size larger than Schneewittchen, Rosa Charm and Alrote Charm; similar to India (not patented, but not as large as Klaus Neubner. The new cultivar is very floriferous, with the flowering appearing above the leaf canopy.

3. Plant shape and growth habit of Tetra Linda are simialr to India and not as compact as Rosa Charm. Schneewittchen, Alrote Charm and Klaus Neubner are not as compact and have a more upright growth habit than Tetra Linda which is more mounded.

4. Leaf and stem color of Tetra Linda is darker green than Rosa Charm; similar to Schneewittchen; but not as dark green as India, Alrote Charm and Klaus Neubner which have reddish stems and reddish infusion on the backs of the leaves.

5. Leaves are thicker than Schneewittchen and Rosa Charm, and similar in thickness to the other comparison cultivars.

6. Stems are stiffer than Schneewitchen and Rosa Charm, and similar in stiffness to the other comparison cultivars.

7. Plants of Tetra Linda are more vigorous than Schneewitchen and better branched; similar in vigor to Klaus Neubner and Alrote Charm but better branching, and similar in branching and vigor to India and Rosa Charm.

8. Leaf size and shape similar to India and Schneewittchen; similar to Klaub Neubner in shape but smaller in size; Rose Charm and Alrote Charm have a narrower longer leaf.

9. Tetra Linda has shorter internodes than Schneewittchen, Klaus Neubner and Alrote Charm, and similar internodes to Rosa Charm and India.

10. Compact vigorous growth with a long flowering period makes Tetra Linda ideal for 10 cm and 15 cm pot plant production. Tetra Linda is relatively late to go into dormancy as days become shorter.

The accompanying color photograph illustrates in perspective view the overall appearance of Tetra Linda, showing colors as true as it is reasonably possible to obtain in a colored reproduction of this type. The photograph was taken in early October.

The following is a detailed description of my new achimenes cultivar based on plant produced under commercial practices in Hannover, Federal Republic of Germany, and Ashtabula, Ohio under greenhouse conditions. Color references are made to The Royal Horticultural Society Color Chart (RHS), except where general colors of ordinary dictionary significance are used.

Parentage:

Mutation of an India that was then doubled by colchicine to produce Tetra Linda.

Propagation:

A. *Stem cutting.*—2–3 cm in length. Time to root: 15 to 18 days at 20° C. summer; 18 to 21 days at 20° C. winter.

B. *Leaf cutting.*—Time to shoot: 4 to 5 weeks at 20° C. summer; 5 to 6 weeks at 20° C. winter.

C. *Rooting habit.*—Numerous, fine, fibrous.

Plant description:

A. *Form.*—Upright, compact, spreading plant. Good basal and self-branching; strong stems hold flowers above foliage; more dense than open.

B. *Habit of growth.*—Multiple shoots develop from base of plant when grown from rhizomes, leaf and stem cuttings, with vegetative shoots from lower leaf axils resulting in a mounded, dense plant.

C. *Foliage.*—Opposite leaves with short internodes, in branches that develop 3 leaves in a whorl. (1) Size: Mature leaves are 45 to 50 mm long and 25 to 30 mm wide. (2) Shape: Ovate. (3) Texture: Upper hirsute, lower pubescent. (4) Margin: Dentate. (5) Color: young foliage, top side 146A; underside 148D with 147D veins; mature foliage, top side 147A; underside 148D, with major veins 147C. (6) Leaf tip: Acute. (7) Leaf base: Acute. (8) Ribs and veins: Pinnate.

Flowering description:

(A) *Flowering habits.*—Flowering occurs in an orderly manner up the stems as the plants develop. Usually both flowers open at the same time from a given node.

(B) *Natural flowering season.*—May to October.

(C) *Form.*—Flowers appear above the leaf canopy mainly because of the long tubular part of the flower.

(D) *Flowers borns.*—A single flower is borne from each leaf axil on a short pedicel. As leaf pairs are added, flowers continue to develop from most axils.

(E) *Flower buds.*—Tubular, approximately 15 mm long with circular flaring at end.

(F) *Permanence of flowers.*—3 to 5 days.

Color:

A. *Upper surface of petals.*—155C white at maturity; when opening under low light and cool temperatures, petal color can be 76C and 84C, fading to white.

B. *Reverse of petals.*—Both newly opened and mature blooms are 155C.

C. *Throat.*—155C.

D. *Discoloration.*—As flower begins to die it starts turning brown.

Petals:

A. *Texture.*—Velvety.

B. *Appearance.*—Fused into a tube for 35 to 40 mm, then 5 heart-shaped petals fused about one-half the way to the edge with the out lobes overlapping mature flower is 50 mm in diameter.

C. *Arrangement.*—3 lower petals come straight out from the tubular part and are slightly larger than the upper 2 petals which are reflexed, making for a circular flat flower.

D. *Persistence.*—3 to 5 days depending on temperature conditions.

E. *Fragrance.*—None.

Reproductive organs:

A. *Stamens.*—4 fertile, 1 sterile. Anther shape: Fused in oblong pairs. Anther color: Brownish. Filament color: Cream white. Pollen color: Cream white.

B. *Pistils.*—Stigma shape: Forked, 3 mm, white. Style color: White (greenish near ovaries). Style size: 30 mm. Ovaries: Numerous, 1–2 mm when immature; greenish color.

Disease resistance: No disease or insect problems noted to date.

I claim:

1. A new and distinct Achimenes plant named Tetra Linda, as illustrated and described, and particularly characterized by its distinct all white flower color, including throat; vigorous and compact growth habit; floriferousness, producing many flowers on stiff stems which elevate the flowers above the leaf canopy; long flowering period, and by its ability to propagate well from rhizomes, leaf and stem cuttings.

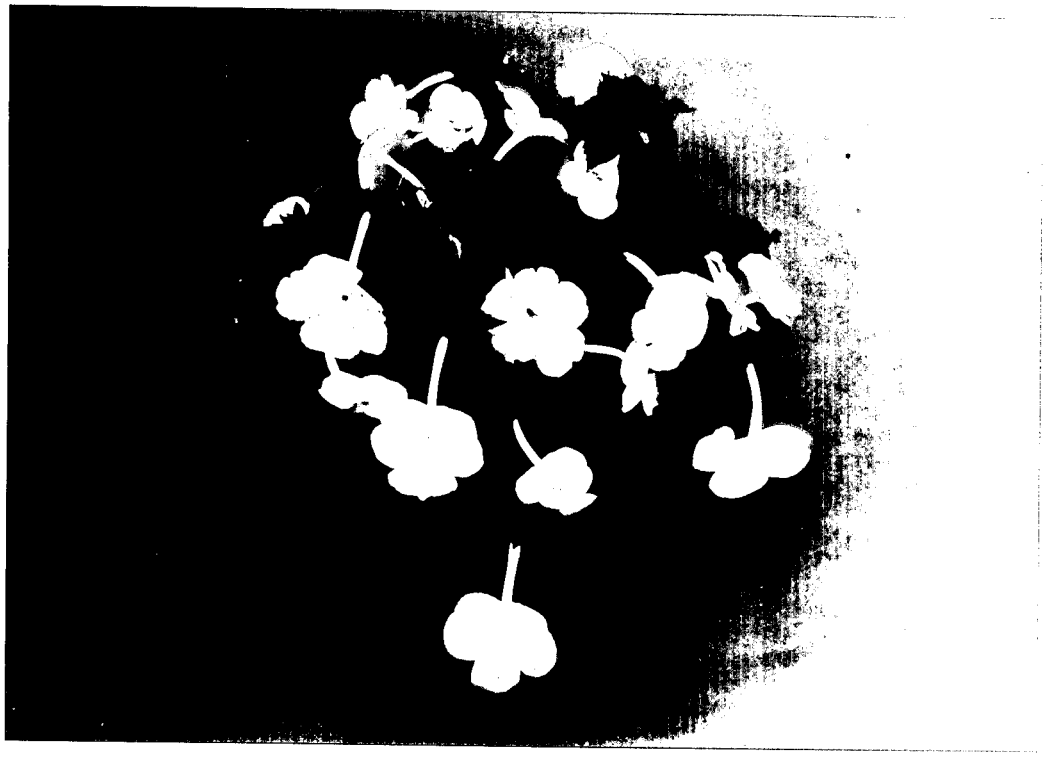

* * * * *